(12) United States Patent
Lee et al.

(10) Patent No.: US 10,242,162 B2
(45) Date of Patent: Mar. 26, 2019

(54) WATER-INSOLUBLE MATERIAL EVALUATION METHOD AND WATER-INSOLUBLE MATERIAL EVALUATION

(71) Applicant: LG Chem, Ltd., Seoul (KR)

(72) Inventors: Seung-Yup Lee, Daejeon (KR); Ji-Won Jeong, Daejeon (KR); Kyoung-Hoon Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/513,636

(22) PCT Filed: Dec. 8, 2015

(86) PCT No.: PCT/KR2015/013410
§ 371 (c)(1),
(2) Date: Mar. 23, 2017

(87) PCT Pub. No.: WO2016/104995
PCT Pub. Date: Jun. 30, 2016

(65) Prior Publication Data
US 2017/0293743 A1 Oct. 12, 2017

(30) Foreign Application Priority Data
Dec. 23, 2014 (KR) .................. 10-2014-0186680

(51) Int. Cl.
*G01N 33/00* (2006.01)
*G06F 19/00* (2018.01)
*G01N 33/15* (2006.01)

(52) U.S. Cl.
CPC .......... *G06F 19/704* (2013.01); *G01N 33/00* (2013.01); *G01N 33/15* (2013.01); *G06F 19/00* (2013.01)

(58) Field of Classification Search
CPC ..... G06F 19/701–19/704; G06F 19/00; G01N 33/00
See application file for complete search history.

(56) References Cited

U.S. PATENT DOCUMENTS

| | | |
|---|---|---|
| 2006/0144171 A1 | 7/2006 | Carlson et al. |
| 2006/0260422 A1 | 11/2006 | Sekizawa et al. |
| 2007/0056119 A1 | 3/2007 | Gardner et al. |
| 2009/0165578 A1 | 7/2009 | Zamloot et al. |
| 2010/0229636 A1 | 9/2010 | Levin et al. |
| 2011/0120239 A1 | 5/2011 | Fetvedt |

(Continued)

FOREIGN PATENT DOCUMENTS

| | | |
|---|---|---|
| CN | 1813054 | 8/2006 |
| CN | 101310282 | 11/2008 |
| CN | 103890132 A | 6/2014 |

OTHER PUBLICATIONS

Machui et al., Solubility, Miscibility, and the Impact on Solid-State Morphology, 2012, Published by Wiley-VCH Verlag GmbH & Co. KGaA, 38 pp.*

(Continued)

*Primary Examiner* — Toan Le
(74) *Attorney, Agent, or Firm* — Lerner, David, Littenberg, Krumholz & Mentlik, LLP

(57) ABSTRACT

This invention relates to a method and system for predictively evaluating a water-insoluble material even without solubility measurement experiments.

7 Claims, 1 Drawing Sheet

(56) References Cited

U.S. PATENT DOCUMENTS

2013/0035923 A1    2/2013  Chen et al.
2014/0230900 A1*   8/2014  Cull .................... H01L 51/0007
                                                    136/263
2014/0348887 A1   11/2014  Hsu et al.

OTHER PUBLICATIONS

Cheng et al., Effect of Solvent Solubility Parameters on the Dispersion of Single-Walled Carbon Nanotubes, 2008, J. Phys. Chem. C, vol. 112, No. 51, pp. 20154-20158.*
International Search Report from PCT/KR2015/013410, dated Mar. 21, 2016.
Stefanis et al., "Prediction of Hansen Solubility Parameters with a New Group-Contribution Method", Int. J. Thermophys, May 13, 2008, vol. 29, pp. 568-585.
Search report from Office Action dated Sep. 4, 2018 in corresponding Chinese Application No. 2015800537940.

\* cited by examiner

WATER-INSOLUBLE MATERIAL EVALUATION METHOD AND WATER-INSOLUBLE MATERIAL EVALUATION

CROSS-REFERENCE TO RELATED APPLICATIONS

The present application is a national phase entry under 35 U.S.C. § 371 of International Application No. PCT/KR2015/013410, filed Dec. 8, 2015, which claims priority from Korean Patent Application No. 10-2014-0186680, filed Dec. 23, 2014, all of which are incorporated herein by reference.

TECHNICAL FIELD

The present invention relates to a method and system for evaluating a water-insoluble material.

BACKGROUND ART

To know the exact values of various properties of organic compounds is regarded as very important in industry and academia because it is crucial to all decisions made throughout production and consumption, including reviewing the validity of the use of the corresponding material, designing synthesis and purification processes, and setting methods and conditions for storage, transportation, use, and disposal. The method of obtaining the most accurate values of properties of an organic compound of interest is also experimentation, but such experimentation, including preparation of the purified sample, the establishment of an environment for accurate measurement, etc., requires considerable cost and time, and is unable to be carried out in some cases. Therefore, as an alternative thereto, many researchers have long tried to predict the exact values of various properties of organic compounds. The prediction of the properties has a long history, and new prediction methods are constantly emerging, and these days, a variety of prediction models, the accuracy and coverage range of which vary depending on the properties, have been devised.

Meanwhile, in the development and separation of new materials using a solution process, it is very important to accurately judge whether a solute, which is a target material, is soluble or insoluble in water.

In this way, the reason why it is important to know whether a solute is water-insoluble is that the solvent that is most frequently used to prepare a solution is water. Also, in the case where a water-soluble material, which is readily dissolved in water, is discharged to the outside, it is not efficiently separated from water, undesirably causing environmental problems. Hence, it is necessary to accurately judge whether a target material is water-insoluble.

A currently useful method of determining whether a target material is water-insoluble is performing a solubility experiment of directly dissolving a target material in water. However, determining whether numerous materials to be tested for new material development are water-insoluble through the solubility experiment is impossible due to time and cost limits.

Particularly in the case where a target material is expensive, a solubility experiment in which a large amount of the material has to be used to determine water insolubility is difficult to carry out. Furthermore, the currently useful experimental method has to be conducted after first actually synthesizing the target material. That is, before the target material is synthesized, the experimental method cannot be applied, making it impossible to determine whether the target material is water-insoluble.

DISCLOSURE

Technical Problem

Accordingly, the present invention has been made keeping in mind the problems encountered in the related art, and the present invention is intended to provide a novel method of evaluating a water-insoluble material, which is able to quantitatively and clearly determine whether a target material is water-insoluble, even without real-world experimentation.

Also, the present invention is intended to provide a method of evaluating a water-insoluble material, in which solubility parameters are calculated using chemical structure information about a material, the water insolubility of which is to be determined, and water insolubility is finally judged based on established quantitative criteria.

Technical Solution

An aspect of the present invention provides a method of evaluating a water-insoluble material, comprising the steps of: (1) selecting N target materials and generating chemical structure information of the target materials; (2) calculating a nonpolar dispersion solubility parameter D, a polar solubility parameter P and a hydrogen-bonding solubility parameter H using the generated chemical structure information; (3) calculating water-insolubility characteristic values of the target materials using Equations 1 and 2 below; and (4) evaluating the calculated water-insolubility characteristic values of the target materials based on quantitative criteria.

$$GIWiS_1[X_i] = \frac{8.7 \times D^{1.2} + 0.45 \times P^{0.8} \times H^{0.4}}{\varepsilon_x} \quad \text{[Equation 1]}$$

$$GIWiS_2[X_i] = \frac{\sqrt{1.2 \times P^2 + 0.8 \times H^2}}{MagT} \quad \text{[Equation 2]}$$

In Equation 1, $\varepsilon_x$ is a real number greater than zero, and in Equation 2, $MagT = \sqrt{D^2+P^2+H^2}$. In Equations 1 and 2, D is a nonpolar dispersion solubility parameter, P is a polar solubility parameter, H is a hydrogen-bonding solubility parameter, $X_i$ is the $i^{th}$ target material, i is a natural number from 1 to N, and N is a natural number.

Another aspect of the present invention provides a system for evaluating a water-insoluble material, including a module using the aforementioned method.

Still another aspect of the present invention provides a recording medium, which is readable by a computer in which a program for executing the aforementioned method is recorded.

Advantageous Effects

In a method of evaluating a water-insoluble material according to the present invention, the water insolubility of a target material can be quantitatively and clearly determined even without real-world experimentation.

In particular, the method of evaluating a water-insoluble material according to the present invention is able to determine whether a target material is water-insoluble even before the actual synthesis thereof.

Furthermore, the present invention, which enables the water-insoluble material to be clearly evaluated even without real-world experimentation, is deemed to be very effective at developing materials using a solution process, solving the related processing problems, and developing an effective separation process.

BEST MODE

Figure 1:
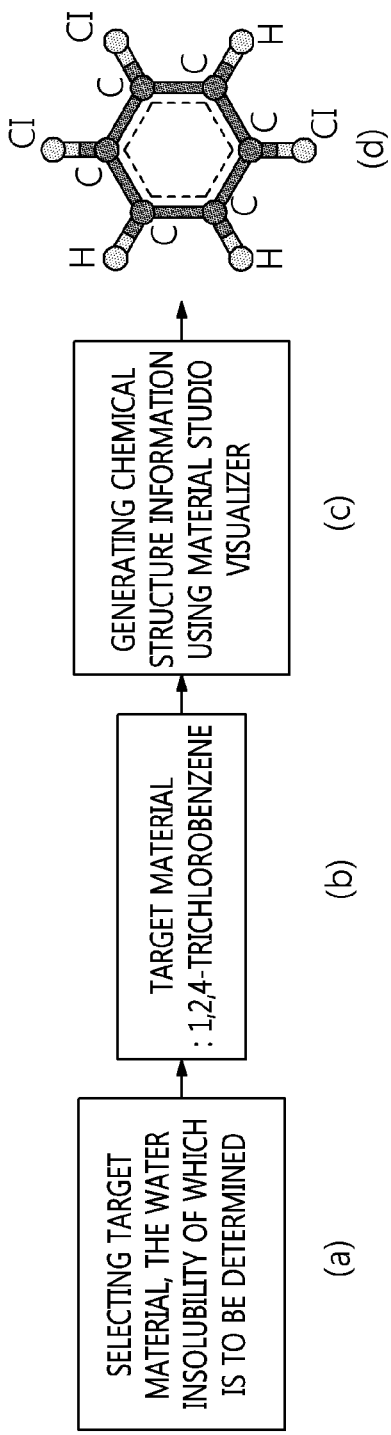
FIG. 1 is a flowchart showing a process step, including selecting target materials, the water insolubility of which is to be determined, and generating chemical structure information of the target materials, according to an embodiment of the present invention.

Hereinafter, a detailed description will be given of the present invention. The following description is merely set forth to illustrate embodiments of the present invention, but is not to be construed as limiting the scope defined by the claims even if it contains restrictive expressions.

As used herein, the term "water-insoluble material" refers to a material that is a solute insoluble in a water solvent.

In order to conventionally determine whether a material is water-insoluble, a solubility experiment is performed in a manner in which a target material is directly dissolved in water. However, determining whether numerous materials to be tested for material development are water-insoluble through such a solubility experiment is impossible due to time and cost limits.

The present inventors have discovered a method of determining whether a target material is water-insoluble without the need to directly synthesize a target material and then perform the solubility experiment, thus culminating in the present invention.

The present invention pertains to GIWiS (Gaugeable Indicator of Water-insoluble Signal). Particularly, the GIWiS method enables the water insolubility of a target material to be finally determined through quantitative criteria established using solubility parameters obtained from chemical structure information of the target material, the water insolubility of which is to be determined.

Specifically, the evaluation method of the present invention includes the steps of (1) selecting N target materials and generating chemical structure information of the target materials; (2) calculating a nonpolar dispersion solubility parameter D, a polar solubility parameter P and a hydrogen-bonding solubility parameter H using the generated chemical structure information; (3) calculating water-insolubility characteristic values of the target materials using Equations 1 and 2 below; and (4) evaluating the calculated water-insolubility characteristic values based on quantitative criteria.

$$GIWiS_1[X_i] = \frac{8.7 \times D^{1.2} + 0.45 \times P^{0.8} \times H^{0.4}}{\varepsilon_x} \quad \text{[Equation 1]}$$

$$GIWiS_2[X_i] = \frac{\sqrt{1.2 \times P^2 + 0.8 \times H^2}}{MagT} \quad \text{[Equation 2]}$$

In Equation 1, $\varepsilon_x$ is a real number greater than zero, and in Equation 2, $MagT = \sqrt{D^2 + P^2 + H^2}$. In Equations 1 and 2, D is a nonpolar dispersion solubility parameter, P is a polar solubility parameter, H is a hydrogen-bonding solubility parameter, $X_i$ is the $i^{th}$ target material, i is a natural number from 1 to N, and N is a natural number.

Below is a description of a method of evaluating a water-insoluble material according to the present invention.

First, step (1) is described below.

In this step, target materials, the water insolubility of which is to be determined, are selected, and chemical structure information of the target materials is generated. Specifically, N target materials, the water insolubility of which is to be determined, are selected, and chemical structure information about the selected N target materials is generated. The chemical structure information represents information about chemical bonding between atoms and molecules of individual target materials.

In a preferred embodiment of the present invention, the number of target materials in step (1) may be set without limitation, so long as it is a natural number. The evaluation method of the invention may be performed regardless of the number of target materials. For example, N is 100 to 1000.

The chemical structure information may be generated using a commonly available program, preferably the Material Studio Visualizer program developed by Accelrys.

FIG. 1 is a flowchart of step (1) according to a preferred embodiment of the present invention. Specifically, when (a) a target material, the water insolubility of which is to be determined, is (b) 1,2,4-trichlorobenzene, (c) the chemical structure information of the target material is generated using Material Studio Visualizer. In the chemical structure generated by the program, (d) C indicates a carbon atom for benzene of an aromatic ring, and Cl and H indicate a chlorine atom and a hydrogen atom, respectively.

Next, step (2) is described.

In this step, solubility parameters are calculated using the generated chemical structure information. Specifically, based on the generated chemical structure information about N target materials, solubility parameters of individual target materials are calculated.

The solubility parameters, obtained through calculation in the present invention, may be classified into three types depending on the characteristics thereof, for example, first, a nonpolar dispersion solubility parameter D based on nonpolarity, second, a polar solubility parameter P based on polarity, and third, a hydrogen-bonding solubility parameter H based on hydrogen bonding.

The solubility parameters may be calculated using any program, so long as the program is commonly available. Preferably, the solubility parameter is calculated using the HSPiP (Hansen Solubility Parameters in Practice) program, developed by C. M. Hansen.

Next, step (3) is described.

In this step, the water-insolubility characteristic values of the target materials are calculated. Specifically, among N target materials, the $i^{th}$ material $X_i$ is calculated for water-insolubility characteristic values, that is, $GIWiS_1[X_i]$ and $GIWiS_2[X_i]$, as defined in Equations 1 and 2 below, using the three solubility parameters calculated in step (2). Here, i is an integer from 1 to N.

$$GIWiS_1[X_i] = \frac{8.7 \times D^{1.2} + 0.45 \times P^{0.8} \times H^{0.4}}{\varepsilon_x} \quad \text{[Equation 1]}$$

$$GIWiS_2[X_i] = \frac{\sqrt{1.2 \times P^2 + 0.8 \times H^2}}{MagT} \quad \text{[Equation 2]}$$

In Equation 1, $\varepsilon_x$ is a real number greater than zero, and in Equation 2, $MagT=\sqrt{D^2+P^2+H^2}$. In Equations 1 and 2, D is a nonpolar dispersion solubility parameter, P is a polar solubility parameter, H is a hydrogen-bonding solubility parameter, $X_i$ is the $i^{th}$ target material, i is a natural number from 1 to N, and N is a natural number.

In a preferred embodiment of the present invention, $\varepsilon_x$ is a scaling factor, and is not particularly limited as long as it is a real number excluding zero, preferably a real number from 0.01 to 332.5, and more preferably 242.2. In Equations 1 and 2 of the present invention, the magnitude of the value may be adjusted through the scaling factor $\varepsilon_x$.

Next, step (4) is described.

In this step, the water insolubility of the target materials is evaluated through quantitative criteria using the water-insolubility characteristic values calculated in step (3). Specifically, the water insolubility of N target materials is finally determined using two established quantitative criteria 1 and 2.

Evaluation of water insolubility may be performed through the following two steps. In the first step, whether $GIWiS_1[X_i]$ and $GIWiS_2[X_i]$, calculated for the $i^{th}$ target material $X_i$ among N target materials, satisfy the following quantitative criterion 1 is evaluated. Here, i is an integer from 1 to N.

The quantitative criterion 1 represents $0.90<GIWiS_1[X_i]$ and $GIWiS_2[X_i]<47.3$. When the $i^{th}$ target material $X_i$ satisfies the quantitative criterion 1, the $i^{th}$ target material $X_i$ is determined to be a water-insoluble material.

In a preferred embodiment of the present invention, when the $i^{th}$ target material $X_i$ satisfies the quantitative criterion 1, whether the $i+1^{th}$ target material $X_{x+1}$ satisfies the quantitative criterion 1 is evaluated when i<N. The evaluation step is repeatedly performed in this way, and is then terminated after the completion of the determination of the water insolubility of N target materials when i=N.

Meanwhile, in the case where the $i^{th}$ target material $X_i$ does not satisfy the quantitative criterion 1, the following second step is applied. In a preferred embodiment of the present invention, when the quantitative criterion 1 is not satisfied, whether $GIWiS_1[X_i]$ and $GIWiS_2[X_i]$, calculated for the $i^{th}$ target material $X_i$ among N target materials, satisfies the following quantitative criterion 2 is evaluated. Here, i is an integer from 1 to N.

The quantitative criterion 2 represents $1.03<GIWiS_1[X_i]$ and $GIWiS_2[X_i]<53.1$. When the $i^{th}$ target material $X_i$ satisfies the quantitative criterion 2, the target material $X_i$ is determined to be a water-insoluble material. In a preferred embodiment of the present invention, when the $i^{th}$ target material $X_i$ satisfies the quantitative criterion 2, whether the $i+1^{th}$ target material $X_{i+1}$ satisfies the quantitative criterion 1 is evaluated when i<N. That is, when the $i^{th}$ target material $X_i$ satisfies the quantitative criterion 2, it is determined to be a water-insoluble material, and then whether the next target material is a water-insoluble material is evaluated. The evaluation step is repeatedly performed in this way, and is then terminated after the completion of the determination of the water insolubility of N target materials when i=N.

On the other hand, in the case where the $i^{th}$ target material $X_i$ does not satisfy the quantitative criterion 2, the $i^{th}$ target material $X_i$ is determined not to be a water-insoluble material. When i<N, whether the $i+1^{th}$ target material $X_{i+1}$ satisfies the quantitative criterion 1 is evaluated. Even when the $i^{th}$ target material $X_i$ does not satisfy the quantitative criterion 2, the water insolubility of the next target material is subsequently evaluated. The evaluation step is repeatedly performed in this way, and is then terminated after the completion of the determination of the water insolubility of N target materials when i=N.

Consequently, in the case where the $i^{th}$ target material $X_i$ of the present invention satisfies neither the quantitative criterion 1 nor the quantitative criterion 2, it is determined not to be a water-insoluble material. The quantitative criterion 2 is able to identify any water-insoluble material that may be missed by the quantitative criterion 1. Therefore, the quantitative criterion 1 and the quantitative criterion 2 have a complementary relationship.

When the method of evaluating the water-insoluble material according to the present invention is applied to typically known water-insoluble materials, it can be confirmed to accurately evaluate water insolubility, thereby ensuring the applicability of the present invention.

In addition, the present invention addresses a system for evaluating a water-insoluble material, including a module using the method of evaluating the water-insoluble material according to the present invention.

In the system for evaluating a water-insoluble material, a description that overlaps that of the method of evaluating the water-insoluble material remains the same.

As used herein, the term "module" refers to a unit that is responsible for a specific function or operation, and may be embodied by hardware and software, either alone or in combination.

In addition, the present invention addresses a recording medium, which is readable by a computer in which a program for executing the method of evaluating the water-insoluble material according to the present invention is recorded.

Mode for Invention

A better understanding of the present invention may be obtained via the following examples, which are set forth to illustrate, but are not to be construed as limiting the scope of the present invention. The scope of the present invention is given by the claims, and also contains all modifications within the meaning and range equivalent to the claims. Unless otherwise mentioned, "%" and "part", indicating amounts in the following examples and comparative examples, are given on a weight basis.

Example (1) Selecting Target Materials, the Water Insolubility of which is to be Determined, and Generating Chemical Structure Information Three target materials Xi (N=3), the water insolubility of which is to be determined, were selected (i=1 to N). The chemical structure information of the three materials was generated using the Material Studio Visualizer program developed by Accelrys. The three target materials Xi are shown in Table 1 below.

TABLE 1

| Target material ($X_i$) | $X_1$ | $X_2$ | $X_3$ |
|---|---|---|---|
| Compound | 1,2,4-trichloro-benzene | Bicyclo[4.4.0]deca-1,3,5,7,9-pentene | Pyrene |

(2) Calculating Solubility Parameters Using the Generated Chemical Structure Information Based on the chemical structure information about the three target materials, solubility parameters were calculated. Here, the solubility was calculated using HSPiP (Hansen Solubility Parameters in Practice). Thereby, three different solubility parameters of each target material, namely a nonpolar dispersion solubility parameter, a polar solubility parameter, and a hydrogen-bonding solubility parameter thereof, were calculated. The calculated solubility values of the target materials are shown in Table 2 below.

TABLE 2

| Target material ($X_i$) | Nonpolar dispersion solubility parameter (D) | Polar solubility parameter (P) | Hydrogen-bonding solubility parameter (H) |
| --- | --- | --- | --- |
| 1,2,4-trichlorobenzene | 20.2 | 4.2 | 3.2 |
| Bicyclo[4.4.0]deca-1,3,5,7,9-pentene | 19.2 | 2.0 | 5.9 |
| Pyrene | 22.7 | 3.6 | 3.7 |

(3) Calculating Water-Insolubility Characteristic Values of Target Materials

Using the three solubility parameters of each of the three target materials $X_i$, calculated in step (2), the water-insolubility characteristics $GIWiS_1$ and $GIWiS_2$, as defined in Equations 1 and 2 below, were calculated.

$$GIWiS_1[X_i] = \frac{8.7 \times D^{1.2} + 0.45 \times P^{0.8} \times H^{0.4}}{\varepsilon_x} \quad \text{[Equation 1]}$$

$$GIWiS_2[X_i] = \frac{\sqrt{1.2 \times P^2 + 0.8 \times H^2}}{MagT} \quad \text{[Equation 2]}$$

In Equation 1, $\varepsilon_x$ was set to 242.2, and in Equation 2, $MagT = \sqrt{D^2 + P^2 + H^2}$. In Equations 1 and 2, D is the nonpolar dispersion solubility parameter, P is the polar solubility parameter, H is the hydrogen-bonding solubility parameter, $X_i$ is the $i^{th}$ target material, i is a natural number from 1 to N, and N is 3. The results are shown in Table 3 below.

TABLE 3

| Target material ($X_i$) | $GIWiS_1$ ($X_i$) | $GIWiS_2$ ($X_i$) |
| --- | --- | --- |
| 1,2,4-trichlorobenzene | 1.33 | 26.0 |
| Bicyclo[4.4.0]deca-1,3,5,7,9-pentene | 1.25 | 28.3 |
| Pyrene | 1.53 | 22.1 |

(4) Evaluating Water Insolubility of Target Materials Based on Quantitative Criteria The water insolubility of the three target materials was finally determined using the two established quantitative criteria 1 and 2.

Quantitative criterion 1: $GIWiS_1[X_i] > 0.90$ and $GIWiS_2[X_i] < 47.3$

Quantitative criterion 2: $GIWiS_1[X_i] > 1.03$ and $GIWiS_2[X_i] < 53.1$

The water-insolubility results, finally determined through the evaluation based on the quantitative criteria 1 and 2, are shown in Table 4 below.

TABLE 4

| Target material ($X_i$) | Results of determination of water insolubility | Basis of determination |
| --- | --- | --- |
| 1,2,4-trichlorobenzene | Water insolubility | Satisfying quantitative criterion 1 |
| Bicyclo[4.4.0]deca-1,3,5,7,9-pentene | Water insolubility | Satisfying quantitative criterion 1 |
| Pyrene | Water insolubility | Satisfying quantitative criterion 1 |

As is apparent from Table 4, for 1,2,4-trichlorobenzene $X_1$, $GIWiS_1[X_1] = 1.33$ and $GIWiS_2[X_1] = 26.0$, and thus it satisfies the quantitative criterion 1, whereby it was finally determined to be a water-insoluble material.

Also, for bicyclo[4.4.0]deca-1,3,5,7,9-pentene $X_2$, $GIWiS_1[X_2] = 1.25$ and $GIWiS_2[X_2] = 28.3$, and thus it satisfies the quantitative criterion 1, whereby it was finally determined to be a water-insoluble material. Also, for pyrene $X_3$, $GIWiS_1[X_3] = 1.53$ and $GIWiS_2[X_3] = 22.1$, and thus it satisfies the quantitative criterion 1, whereby it was finally determined to be a water-insoluble material.

Comparative Example 2-butanol was used as the target material $X_4$, and (1) chemical structure information thereof was generated and (2) solubility parameters thereof were calculated in the same manner as in the above Example. The calculated nonpolar dispersion solubility parameter, polar solubility parameter and hydrogen-bonding solubility parameter of the target material $X_4$, that is, 2-butanol, were 15.8, 5.7 and 14.5, respectively.

(3) The water-insolubility characteristic values of 2-butanol, as the target material $X_4$, were calculated in the same manner as in the above Example.

Finally, (4) the water insolubility of 2-butanol, as the target material $X_4$, was evaluated in the same manner as in the above Example.

As results thereof, for 2-butanol, as the target material $X_4$, $GIWiS_1[X_4] = 1.01$ and $GIWiS_2[X_4] = 64.9$, whereby it is thus found to satisfy neither the quantitative criterion 1 nor the quantitative criterion 2.

Therefore, 2-butanol, as the target material $X_4$, was finally determined not to be a water-insoluble material.

Test Example

In order to evaluate the validity of the method of determining the water insolubility according to the present invention in the Example and Comparative Example, the following testing was performed.

The above four target materials $X_1$, $X_2$, $X_3$ and $X_4$ were dissolved in 100 g of water at 25° C. and 1 atm for 24 hr, and the solubility thereof was measured.

As results thereof, all three target materials $X_1$, $X_2$ and $X_3$ of the Example were dissolved in amounts of 0.005 g or less, and thus the water solubility thereof approximated zero. In contrast, the target material $X_4$ of the Comparative Example was dissolved in an amount of 30 g, and thus the water solubility thereof was determined to be very high.

Therefore, all three target materials of the Example were determined to be water-insoluble materials, and the target material of the Comparative Example was determined not to be a water-insoluble material.

In conclusion, the method of evaluating water insolubility using GIWiS according to the present invention can be found to accurately determine the water insolubility of a material even without real-world experimentation for solubility measurement.

The invention claimed is:

1. A method of determining water insolubility of a material even without real-world experimentation for solubility measurement, comprising steps of:
   (1) selecting N target materials and generating chemical structure information about chemical bonding between atoms and molecules of the target materials;
   (2) calculating a nonpolar dispersion solubility parameter (D), a polar solubility parameter (P) and a hydrogen-bonding solubility parameter (H) of the target materials using the generated chemical structure information;
   (3) calculating water-insolubility characteristic values of the target materials using Equations 1 and 2 below; and
   (4) evaluating the calculated water-insolubility characteristic values, GIWiS (Gauge-able Indicator of Water-insoluble Signal value) of the target materials based on quantitative criteria:

$$GIWiS_1[X_i] = \frac{8.7 \times D^{1.2} + 0.45 \times P^{0.8} \times H^{0.4}}{\varepsilon_x} \quad \text{[Equation 1]}$$

$$GIWiS_2[X_i] = \frac{\sqrt{1.2 \times P^2 + 0.8 \times H^2}}{MagT} \quad \text{[Equation 2]}$$

in Equation 1, $\varepsilon_x$ is a real number greater than zero,
in Equation 2, $MagT = \sqrt{D^2 + P^2 + H^2}$, and
in Equations 1 and 2, D is a nonpolar dispersion solubility parameter, P is a polar solubility parameter, H is a hydrogen-bonding solubility parameter, $X_i$ is an $i^{th}$ target material, i is a natural number from 1 to N, and N is a natural number;

wherein in the step (4), the $i^{th}$ target material ($X_i$) is determined to be a water-insoluble material when satisfying a quantitative criterion 1 of $0.9 < GIWiS_1[X_i]$ and $GIWiS_2[X_i] < 47.3$, and wherein the $i^{th}$ target material ($X_i$) is determined to be a water-insoluble material when satisfying a quantitative criterion 2 of $1.03 < GIWiS_1[X_i]$ and $GIWiS_2[X_i] < 53.1$, without satisfying the quantitative criterion 1.

2. The method of claim 1, wherein in the step (3), $\varepsilon_x$ of Equation 1 is a real number from 0.1 to 332.5.

3. The method of claim 1, wherein, when the $i^{th}$ target material ($X_i$) satisfies the quantitative criterion 1, whether an $i+1^{th}$ target material ($X_{i+1}$) satisfies the quantitative criterion 1 is evaluated when i<N, and the evaluating is terminated when i=N.

4. The method of claim 1, wherein when the $i^{th}$ target material ($X_i$) is found to satisfy or not satisfy the quantitative criterion 2, whether an $i+1^{th}$ target material ($X_{i+1}$) satisfies the quantitative criterion 1 is evaluated when i<N, and the evaluating is terminated when i=N.

5. The method of claim 1, wherein the step (2) is performed using an HSPiP (Hansen Solubility Parameters in Practice) program.

6. A system for evaluating a water-insoluble material, comprising a module using the method of claim 1.

7. A recording non-transitory computer readable medium, which is readable by a computer in which a program for executing the method of claim 1 is recorded.

* * * * *